United States Patent
Wegmuller et al.

(10) Patent No.: US 7,847,264 B2
(45) Date of Patent: Dec. 7, 2010

(54) METHOD OF MEASURING THE COLOUR OF PRINTED SAMPLES CONTAINING BRIGHTENERS

(75) Inventors: Mark Wegmuller, Zurich (CH); Peter Ehbets, Zurich (CH); Beat Frick, Tufistrasse (CH)

(73) Assignee: X-Rite Europe GmbH, Regensdorf (CH)

( * ) Notice: Subject to any disclaimer, the term of this patent is extended or adjusted under 35 U.S.C. 154(b) by 121 days.

(21) Appl. No.: 12/136,373

(22) Filed: Jun. 10, 2008

(65) Prior Publication Data

US 2008/0308740 A1  Dec. 18, 2008

(30) Foreign Application Priority Data

Jun. 13, 2007  (EP) .................................. 07110191

(51) Int. Cl.
*G01J 1/42* (2006.01)

(52) U.S. Cl. ..................................... 250/372

(58) Field of Classification Search ................ 250/372, 250/461.1; 356/405, 72, 319, 446, 326, 328, 356/317, 318

See application file for complete search history.

(56) References Cited

U.S. PATENT DOCUMENTS 5,636,015 A * 6/1997 Imura et al. .................... 356/72
2002/0135768 A1 * 9/2002 Sugiyama et al. ........... 356/405
2006/0192957 A1 * 8/2006 Frick et al. ................... 356/328
2007/0086009 A1 4/2007 Ehbets et al.

FOREIGN PATENT DOCUMENTS

JP  2006084333  3/2006

OTHER PUBLICATIONS

Klaus Witt, "Colorimetric control of photographic prints: the problem of fluorescence," 2002, Proceedings of SPIE, vol. 4421, pp. 777-780.*
European Search Report dated Oct. 26, 2007.

* cited by examiner

*Primary Examiner*—David P Porta
*Assistant Examiner*—Kiho Kim
(74) *Attorney, Agent, or Firm*—McCarter & English, LLP

(57) ABSTRACT

Methods for measuring the colour of printed samples by measuring a first spectral proportion of the total spectral reflection factor of a sample by illuminating the sample with light having no UV element are provided. The methods calculate a spectral correction factor by making allowance for the characterisation data of the brightened substrate and the spectral properties of a selected type of illuminating light, adding the spectral correction factor to the first spectral proportion to obtain the total spectral reflection factor of the measured sample. The methods further evaluate the total spectral reflection factor on the basis of measurements taken with illuminating light with no UV element and with UV light only on a limited set of measurement samples, especially on the non-printed substrate only (paper whiteness).

19 Claims, 3 Drawing Sheets

METHOD OF MEASURING THE COLOUR OF PRINTED SAMPLES CONTAINING BRIGHTENERS

BACKGROUND

1. Technical Field

The present invention relates to methods for measuring colour. More particularly the present invention involves measuring the colour of samples printed on substrates containing brighteners.

2. Background Art

Optical brighteners are often used in the production of papers. Optical brighteners can improve the degree of whiteness of the paper (generally substrate) and reduce manufacturing costs.

Optical brighteners absorb light in the ultraviolet (UV) wavelength range from 320 to 410 nm and re-emit fluorescent light in the visible blue spectral range between 420 and 550 nm. The maximum of the fluorescent spectrum is between 430 and 440 nm.

The effect of optical brighteners and the resultant colour of the paper are influenced to a large degree by the spectral distribution of the illuminating light, primarily due to the ratio of the light levels in the UV and in the blue spectral range. The colour reproduced by printed samples is additionally influenced by the absorption behaviour of the colour coating on the paper substrate.

The non-linear behaviour of optical brighteners places high demands on colour measuring technology. The objectives of colour measuring technology are to obtain measurement values which correlate well with a specific visual observation condition with a defined lighting spectrum on the one hand. In terms of the process control and exchange of measurement data, on the other hand, it is important that different measuring devices output measurement values that are as far as possible identical on the same samples.

The current situation in colour measuring technology is satisfactory for printed samples on substrates containing no optical brighteners. If, however, optical brighteners are used, higher unsatisfactory variances are observed in colour measurement values.

In order to correctly adapt measuring devices for substrates containing brighteners, it is important that the lighting spectra in the devices have identical relative distributions in the UV range and in the blue spectral range. This is because higher variances between measuring devices occur primarily in the UV range.

Furthermore, In order to obtain compatibility with visual observation, it is necessary that the lighting conditions in the device be identical to those for visual observation. In technical terms, this congruence is very difficult to achieve since external light conditions are variable.

Current hand-held colour measuring devices, such as the SpectroEye made by Gretag Macbeth AG, use a glow lamp as the light source. The SpectroEye device has a filter wheel in the measuring optics. The lighting spectrum and receiver characteristic can be modified using different measuring filters. To obtain good conformance of the device, it is recommended that brightened samples be measured using the in-built UV blocking filter. This filter eliminates the UV element of the illuminating light so that the optical brightener is not able to generate any fluorescence. This eliminates the requirements for exact control of the lighting spectrum. The problem with the UV block filter method, however, is the fact that the measurement values do not match the real observation conditions because typical light sources usually contain a UV element and thus excite the brighteners.

It is possible to obtain exact measurement results with what is known as the bi-spectral measuring method. A bi-spectral measuring device has a monochromator in the lighting optics and a spectral analyser in the receiver channel. The measurement takes place sequentially. A complete reflection spectrum is measured for every lighting wavelength and stored in matrix format. The resultant reflection spectrum for the sample is determined by multiplying the matrix by a vector which contains the spectral optical energy distribution of the required light type. There is no restriction on this measuring technique; however, the sequential measuring procedure is time-consuming. Furthermore, the measurement technique is expensive to set up and is therefore impractical for use on an industrial scale. Examples of bi-spectral measuring systems include the BFC-450 device made by the Labsphere company and the CM-3800 made by Minolta.

US patent specification No. 6844931 describes a colour measuring system with lighting using variable light-emitting diodes (LED) and a spectral analyser in the receiver. The LED light source comprises a plurality of differently coloured, white and UV LEDs. The individual LEDs can be individually activated so that the spectral light distribution can be electronically adapted to a desired spectrum. The spectral reflection factor of the sample is then determined with an individual measurement using the desired lighting spectrum.

US patent application No. 2007/0086009 A1 (EP 1775565 A1) describes a method of determining the reflection spectrum of the sample using a double measurement. In the first measurement, the reflection spectrum is determined using the known UV block filter technique. In the second measurement, only UV light is used for the lighting and the fluorescence spectrum is measured separately. By adding the correctly weighted spectra accordingly, it is then possible to output the reflection factor for any type of excitation light. One disadvantage of this method is the fact that every sample has to be measured twice.

Against the background of this prior art, an objective of the invention is to provide a method of measuring the colour of brightened samples which makes it possible to determine the total spectral reflection factor of the sample for desired target light types quickly and obviates the need for double measurements, which can be implemented easily and inexpensively using existing colour measuring devices at the same time. The objectives underlying the invention are achieved as described herein.

SUMMARY

The present invention proposes a method for measuring the colour of samples printed on substrates containing brighteners. More particularly the proposed method, generally, includes the steps of (i) determining a total spectral reflection factor of a sample printed on a substrate containing a brightener and (ii) making the total spectral reflection factor available for calculating values characterising the colour of the sample. The sample may include one or more colour layers.

In exemplary embodiments, the total spectral reflection factor is determined as the sum of a first spectral proportion (RUVblock($\lambda$)) and a spectral correction factor (RiUVpass ($\lambda$)). The first spectral proportion represents a spectral reflection factor of the sample determined during illumination with light consisting essentially of UV-free light. The spectral correction factor represents only a proportion of the total spectral reflection factor of the sample determined by the effect of fluorescence of the brightener. Note that the spectral correction factor is calculated allowing for characterisation data of: (i) the substrate and the brightener contained in the substrate, and (ii) the spectrum of a selected type of lighting ($E_i(\lambda)$) from the first spectral proportion.

Against the background of the prior art, the objective of the present invention is to propose a method of measuring the colour of brightened samples, which makes it possible to determine the total spectral reflection factor of the sample for desired target light types quickly and obviates the need for double measurements. The proposed method can be implemented easily and inexpensively using existing colour measuring devices.

Additional features, functions and benefits of the disclosed apparatus, systems and methods will be apparent from the description which follows, particularly when read in conjunction with the appended figures.

BRIEF DESCRIPTION OF THE DRAWINGS

The invention will be described in more detail below with reference to the appended drawings. Of these.

DESCRIPTION OF EXEMPLARY EMBODIMENTS

As will be explained in more detail below, in addition to the measurements in the visible range, it is also necessary to take several (a few) measurements in the UV range for the purpose of the measuring method proposed by the invention. These measurements may be taken with separate measuring devices but it is also possible to use one measuring device which is designed for taking measurements in both ranges.

Figure 1:
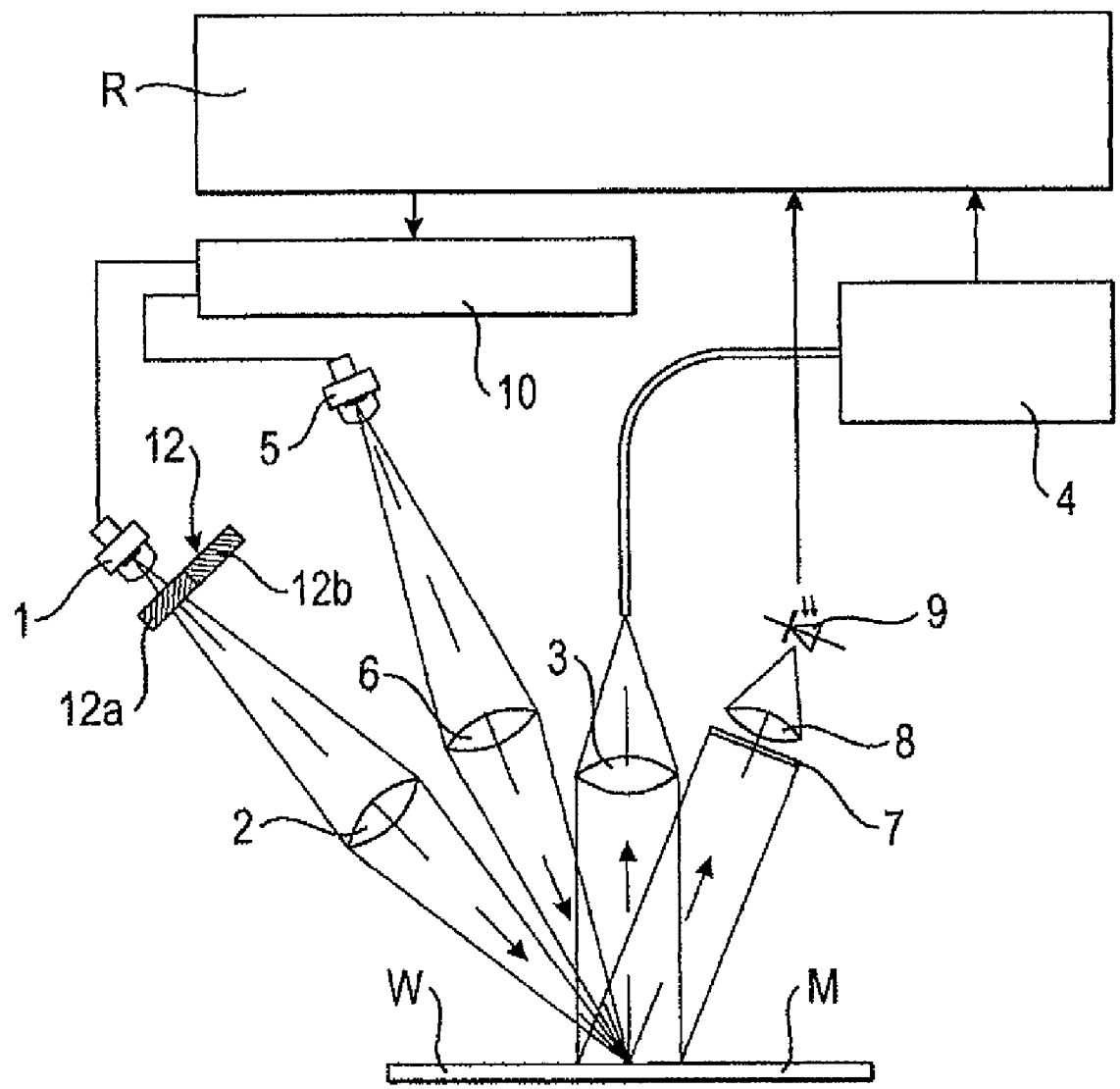
FIG. 1 is a schematic diagram illustrating the most important components of a measuring device suitable for the measuring method proposed by the invention.

With initial reference to FIG. 1, an exemplary measuring device for taking measurements in both ranges is depicted. The measurement device is advantageously suited for the measuring method described herein. Full details of the measurement device and its calibration are given in the aforementioned US patent application No. 2007/0086009 which is hereby incorporated in its entirety. The measurement device is briefly explained with reference to FIG. 1. Specifically, the measuring device comprises a first light source 1, first lighting optics 2, first pick-up optics 3, a first photoelectric converter 4, a second light source 5, second lighting optics 6, a UV filter 7, second pick-up optics 8, a second photoelectric converter 9, a lamp controller 10 and a computer R for controlling the photoelectric converters and for digitising and further processing and storing the measurement signals generated by the photoelectric converters. The first light source 1, first lighting optics 2, first pick-up optics 3 and first converter 4 together form a first measuring arrangement of a known type, which illuminates a measurement object M or sample at an angle of incidence of 45° and picks up the measurement light returned by the measurement object at an angle of reflection of 0°. Likewise, the second light source 5, second lighting optics 6, the UV filter 7, second pick-up optics 8 and second converter 9 form a measuring arrangement which is also known, in this instance with a symmetrical measuring geometry, where the angle of incidence of the lighting and angle of reflection of the returned measurement light is 30° in each case, for example.

For the first light source 1, a light source is typically used which has a continuous emission spectrum across the UV and visible spectral range. Xenon arc lamps or glow lamps are often used. The first photoelectric converter 4 is preferably designed as a spectral analyser, which is sensitive as a minimum across the visible spectral range from 400 to 700 nm. In a manner known per se, the spectral analyser may be a spectrometer or colorimeter. As mentioned above, the first measuring arrangement satisfies the geometric measuring conditions of the normalised 45°/0° geometry.

In a different design of the measuring device, a displaceable filter arrangement 12 is provided in the optical path of the light of the first measuring arrangement, which is transparent either to visible light only or to UV light only, depending on the setting. The filter arrangement used may be a filter wheel, for example, with two appropriate filters, such as used in the known SpectroEye device mentioned above. One of the two filters 12a of the filter arrangement 12 is a UV blocking filter in the form of an edge filter, which suppresses illuminating light below 400 nm and has a good transmission across the visible range. The other filter 12b of the filter arrangement 12 is a complementary edge filter which suppresses light with a wavelength above 400 nm and is as readily transparent to UV light as possible. This filter (UV transmission filter) may also be designed so that it enables the lighting spectrum in the UV range to be better adapted to a desired type of reference light.

Alternatively, in a different embodiment of the measuring device, a UV/non-UV double illumination system which can be switched accordingly may be set up by means of two or more different light sources which can be switched on and off individually. This being the case, some of the light sources should emit light in the UV range only and the other ones of the light sources should emit light in the visible range only. This can be achieved using continuous light sources with stationary filters placed in front of them. Alternatively, light sources may be used which have a spectrally limited emission spectrum without additional filtering. Typical light sources of this type are light-emitting diodes (LEDs). For example, the UV-LEDs NCCU033(T) and NCCU001E made by Nichia with peak wavelengths of 365 nm respectively 380 nm may be used individually or in combination as the UV light source. The UV blocking filter characteristic may be achieved using white LEDs, such as those sold by the manufacturer Lumileds under the product name Luxeon for example. These white LEDs have a continuous emission spectrum in the range of 420 nm to 700 nm. In FIG. 1, this implementation option for double illumination with controlled light sources is symbolised by the second measuring arrangement 5-9. Naturally, in this instance, the filter arrangement 12 is then superfluous.

Lighting and measuring with UV light does not have to conform to the 45°/0° geometry and the measurement light may be applied to the measurement object at any angle. If separate light sources are used for the UV light and the visible light, it is therefore possible to dispose the UV light sources at an angle of less than 45°, for example approximately 30°, thereby enabling a more compact construction of the measuring device to be obtained.

The measuring device also has a white reference standard W, which is calibrated for the absolute reflection factor. In a manner known per se, the white reference standard may comprise a white ceramic tile which has been calibrated with a calibrated reference spectral photometer. When taking measurements on the white reference standard W, the latter takes the place (in a known manner) of the actual measurement object M.

It is also necessary for the measuring device to have a UV reference channel for the UV light source, the purpose of which is to monitor the light level of the UV source during the service life of the device and detect any fluctuations in the level. The measuring system makes allowance for any fluctuations in level when computing the measurement values. The UV reference channel may be set up using the spectral photoelectric converter 4 if it is sensitive in the UV range and the white reference standard W has an adequate reflection factor in the UV range. Alternatively, the UV reference channel may be set up using a photodiode (converter 9) which is sensitive in the UV range and measures the light reflected by the white reference standard. A third option for setting up the UV reference channel is to incorporate a fluorescent sample which is excited in the UV range and generates light in the visible range. The visible fluorescent element can then be measured with the spectral receiver (converter 4). Suitable fluorescence standards are sold by Labsphere under the product name Spectralon.

In order to take the measurements, the receiver channel (formed by the pick-up optics and the spectral converter) is radiometrically calibrated. The radiometric calibration is run in a manner known per se by measuring a continuous light source with a known spectral signal distribution (reference spectrum) by means of the receiver channel. In a known manner, the radiometric calibration is based on the quotient of the reference spectrum by the corresponding digitised (spectral) measurement values of the receiver.

Figure 2:
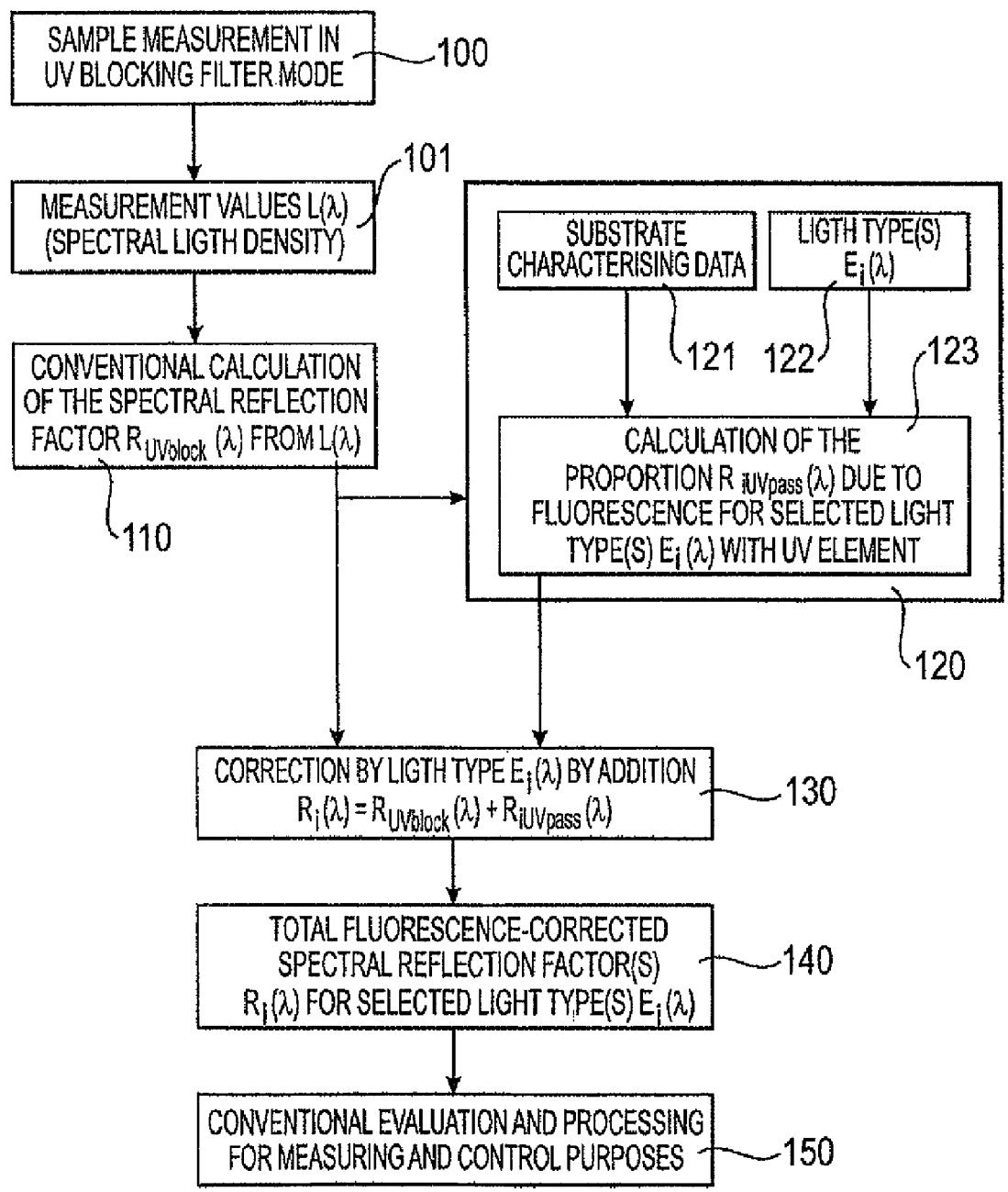
FIG. 2 is a block diagram illustrating an example of an embodiment of the measuring method proposed by the invention and FIG. 3 is a block diagram of the correction calculation used in the measuring method proposed by the invention illustrated in FIG. 2.

With reference now to FIG. 2 an exemplary measuring method of the present invention is illustrated. The exemplary method of FIG. 2 is based on the measurement configuration depicted in FIG. 1. However, the measuring method proposed by the present invention may be adapted to all other common measuring systems and/or measuring devices. The expression, "measuring in UV blocking filter mode", as used herein, indicates a measurement using illumination lighting with or without an infinitesimal UV element. Similarly, the expression "measuring in UV pass filter mode" as used herein, indicates a measurement using illumination lighting consisting essentially of UV light. The UV blocking filter mode is set up by lighting with a white light-emitting diode with an infinitesimal UV element for example, while the UV pass filter mode uses lighting with a pure UV light-emitting diode, for example.

FIG. 2 illustrates the basic sequence of the measuring method proposed by the invention. The basic elements included in FIG. 2 are summarized below:

100 Sample measurement in UV blocking filter mode
101 Measurement values $L(\lambda)$ (spectral light density)
110 Conventional calculation of the spectral reflection factor $R_{UVblock}(\lambda)$ from $L(\lambda)$
121 Substrate characterising data
122 Light type(s) $E_i(\lambda)$
123 Calculation of the proportion $R_{iUVpass}(\lambda)$ due to fluorescence for selected light type(s) $E_i(\lambda)$ with UV element
130 Correction by light type $E_i(\lambda)$ by addition $R_i(\lambda)=R_{UVblock}(\lambda)+R_{iUVpass}(\lambda)$
140 Total fluorescence-corrected spectral reflection factor(s) $R_i(\lambda)$ for selected light type(s) $E_i(\lambda)$
150 Conventional evaluation and processing for measuring and control purposes The measurement object (sample) is spectrally measured (box 100) in the UV blocking filter mode (only) and the measurement values determined during this process represent the spectral light density $L(\lambda)$ of the sample at the measurement site (box 101). From the spectral light density $L(\lambda)$, the spectral reflection factor $R_{UVblock}(\lambda)$ of the sample is determined (box 110) in a known manner (using the white calibration mentioned above). This spectral reflection factor $R_{UVblock}(\lambda)$ represents a first spectral portion of the total spectral reflection factor of the sample. A spectral correction element or correction factor computed as proposed by the invention is then added (box 130) to this spectral reflection factor $R_{UVblock}(\lambda)$, which represents the portion $R_{iUVpass}(\lambda)$ of the total spectral reflection factor caused by the brightener of the substrate of the measurement object due to fluorescence when illuminated with UV light. The result of this (additive) correction is finally the total spectral reflection factor $R_i(\lambda)$ (box 140). The calculation of the spectral correction factor is indicated as a whole by box 120 in FIG. 2. The total spectral reflection factor $R_i(\lambda)$ can then be evaluated or further processed (box 150) in a known manner for measurement and control purposes. One evaluation option is to compute and optionally display the colour values of the sample, for example.

The proportion $R_{iUVpass}(\lambda)$ of the total spectral reflection factor caused by the brightener of the substrate of the measurement object due to fluorescence when illuminated with the UV element primarily depends on the substrate of the measurement object, i.e. on the brightener contained in it and on the type of light (spectral composition) of the illuminating light for which the proportion has to be determined. As a rule, different proportions $R_{iUVpass}(\lambda)$ occur for different light types i. The proportion is also influenced by the additional absorption in the colour coating and by the surface effects at the measurement site. The brightener is normally embedded in the substrate but may also be contained in a coating (e.g. clear varnish coating) of the substrate, which in this case is itself free of brightener. The measuring method proposed by the invention is also suitable for substrates brightened in this manner.

In order to calculate the proportion $R_{iUVpass}(\lambda)$ due to fluorescence, the characteristic data (spectral properties) of the substrate or the brightener used must be known. This is either made available by the substrate manufacturer or by taking preparatory (one-off) measurements. Further explanation of this will be given below. The characterising data of the substrate is symbolised by box 121 in FIG. 2.

The types of lighting for which the fluorescence correction has to be computed must likewise be determined. This is indicated by box 122 in FIG. 2. The light types are usually defined by emission spectra $E_i(\lambda)$, where the index i stands for an individual type of light. Accordingly, the index i in the proportion $R_{iUVpass}(\lambda)$ refers to an individual light type i. The light types might be the standard light types set out in CIE (e.g. D50 or A) or any other types of light specific to the application, for example.

One of the major advantages of the measuring method proposed by the invention is that the fluorescence correction can not only be determined for a given light type but for any and also several light types. The light type $E_i(\lambda)$ in question or several light types $E_i(\lambda)$ in question is or are selected (box 122) at the start of the measurement or alternatively subsequently after the measurement, and the associated fluorescence correction $R_{iUVpass}(\lambda)$ is calculated for every selected light type so that in the end, an associated total spectral reflection factor $R_i(\lambda)$ is available (box 140) for every selected light type $E_i(\lambda)$. The total spectral reflection factor $R_i(\lambda)$ obtained from the sum of the spectral reflection factor $R_{UVblock}(\lambda)$ measured in UV blocking filter mode and the proportion $R_{iUVpass}(\lambda)$ due to fluorescence corresponds to the spectral reflection factor measured with a (filterless) measuring device of the respective illuminating light type.

As explained above, the fluorescence correction or spectral proportion $R_{iUVpass}(\lambda)$ is calculated from the characterising data of the substrate (box 121); the spectral data of the selected light type $E_i(\lambda)$ (box 122) and the measurement values of the sample (spectral light density $L(\lambda)$, box 101) on the basis of a model symbolised by box 123 in FIG. 2. An exemplary model (box 123) is explained in more detail with reference to FIG. 3.

Figure 3:
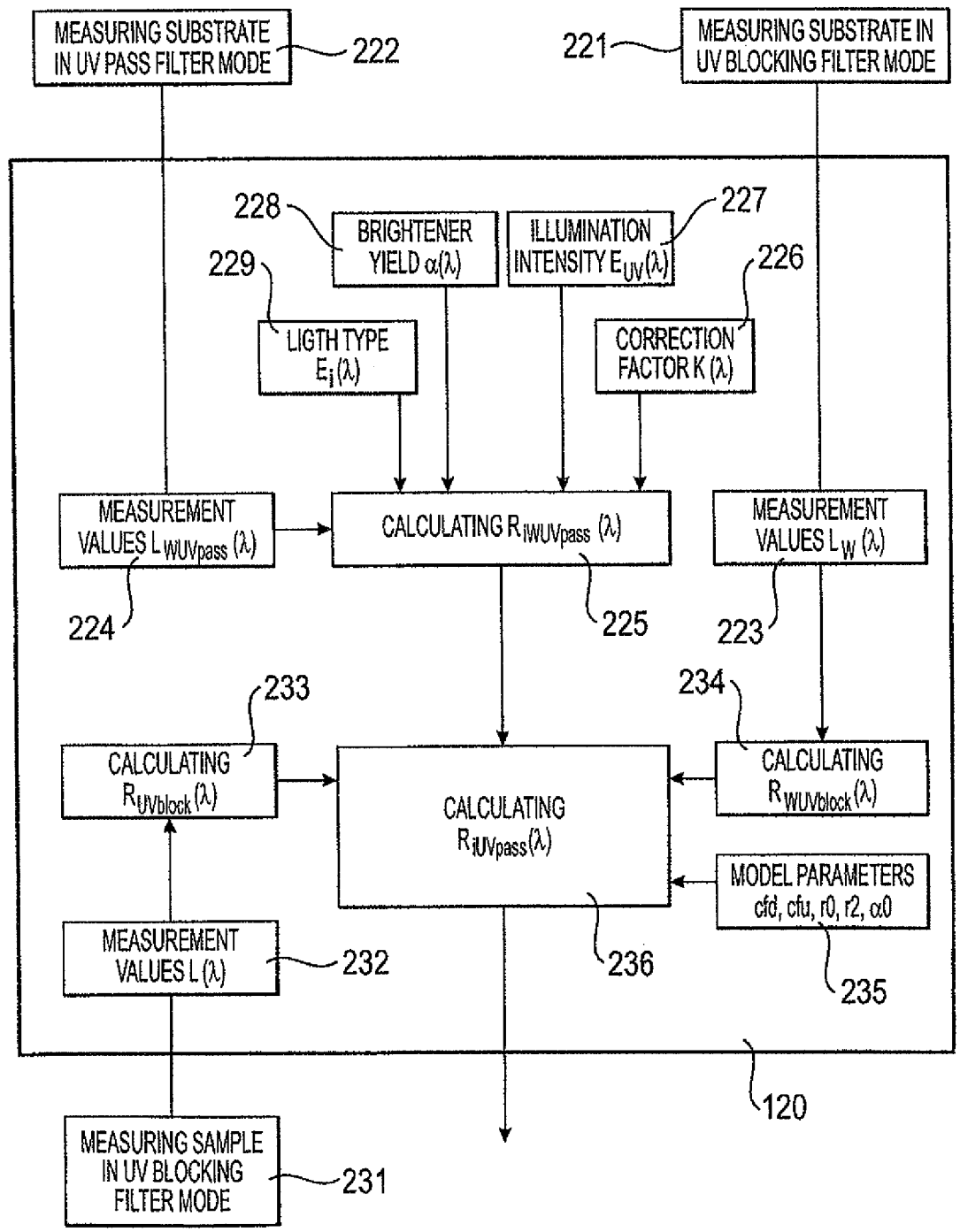

The basic elements of the exemplary model depicted in FIG. 3 are summarized below:

- 222 Measuring substrate in UV pass filter mode
- 221 Measuring substrate in UV blocking filter mode
- 228 Brightener yield $\alpha(\lambda)$
- 227 Illumination intensity $E_{UV}(\lambda)$
- 229 Light type $E_i(\lambda)$
- 226 Correction factor $K(\lambda)$
- 224 Measurement values $L_{WUVpass}(\lambda)$
- 225 Calculating $R_{iWUVpass}(\lambda)$
- 223 Measurement values $L_W(\lambda)$
- 233 Calculating $R_{UVblock}(\lambda)$
- 236 Calculating $R_{iUVpass}(\lambda)$
- 234 Calculating $R_{WUVblock}(\lambda)$
- 232 Measurement values $L(\lambda)$
- 235 Model parameters cfd, cfu, r0, r2, $\alpha$0
- 231 Measuring sample in UV blocking filter mode In the variant of the calculation of the fluorescence correction factor $R_{iUVpass}(\lambda)$ illustrated as an example in FIG. 3, the substrate characterising data used is obtained from the measurements carried out on the non-printed substrate (paper whiteness) of the measurement object prior to measuring the sample. As will be explained below, however, the measuring method proposed by the invention may also be easily adapted to substrate characterisation data from a different origin.

Prior to the actual sample measurement on a printed colour field of the substrate, the substrate of the measurement object is measured at a non-printed point (paper whiteness) both in the UV blocking filter mode and in the UV pass filter mode (boxes 221 and 222). The spectral reflection factor $R_{WUVblock}(\lambda)$ is determined (box 234) from measurement values (spectral light density) $L_W(\lambda)$ (box 223) obtained in a known manner in the UV blocking filter mode. The correction factor $R_{iWUVpass}(\lambda)$ due to fluorescence is calculated (box 225) from the measurement values (spectral light density) $L_{WUVpass}(\lambda)$ in UV pass filter mode (box 224) using the formula $$R_{iWUVpass}(\lambda) = \frac{K(\lambda) \cdot L_{WUVpass}(\lambda) \cdot \pi}{E_i(\lambda)} * \frac{\int d\lambda \cdot \alpha(\lambda) \cdot E_i(\lambda)}{\int d\lambda \cdot \alpha(\lambda) \cdot E_{UV}(\lambda)} \quad \text{[Formula 1]}$$

(The index W denotes the measurement on the substrate or paper whiteness).

In the formula:

$E_i(\lambda)$ means the spectral illumination intensity of the light type(s) "i" at the measurement site, $E_{UV}(\lambda)$ means the spectral illumination intensity of the UV illumination at the measurement site, $\alpha(\lambda)$ means the spectral yield of the brightener in the substrate, $L_{WUVpass}(\lambda)$ means the measurement values determined on the substrate in UV pass filter mode and $K(\lambda)$ means a spectral correction factor for corrections of the second order.

$K(\lambda)$ and $E_{UV}(\lambda)$ are data specific to the measuring device which are determined and stored (boxes 226 and 227) when setting up and calibrating the measuring device that will be used.

$K(\lambda)$ corrects inadequacies of the calibration and of the correction model. It is determined empirically by measurements taken on a known brightened reference sample and is determined so that the calculated total spectral reflection factor of the reference sample matches the total spectral reflection factor measured with the same light type by means of a reference measuring device.

$\alpha(\lambda)$ is selected as being identical for all substrates because the brighteners commonly used exhibit a very similar absorption behaviour. A bell-shaped curve is typically used as the basis with a central value of around 375 nm and a full width at half maximum (FWHM) of around 80 nm. However, it would also be possible to measure a typical brightener or use the relevant manufacturer's data (box 228).

$E_i(\lambda)$ may be selected by the user, e.g. from the CIE standard light types or from an experimentally measured light type (e.g. a light box). As demonstrated by formula 1, the absolute scaling of $E_i(\lambda)$ is identical as a result and only the relative spectral weighting is decisive (box 229).

The reflection factor $R_{WUVblock}(\lambda)$ and the calculated correction factor $R_{iWUVpass}(\lambda)$ are added to obtain the total spectral reflection factor $R_{iW}(\lambda0$ for the non-printed substrate (paper whiteness):

$$R_{iW}(\lambda) = R_{WUVblock}(\lambda) + R_{iWUVpass}(\lambda) \quad \text{[Formula 2]}$$

In a manner similar to formula 2, the total spectral reflection factor of the actual measurement at printed points (colour fields) of the measurement object are computed. The index W has been deliberately omitted below and in order to give a better overall view, the dependency on wavelength is no longer specifically given. This simplified notation results in:

$$R_i = R_{UVblock} + R_{iUVpass} \quad \text{[Formula 3]}$$

The total spectral reflection factor $R_i$ for the measured colour field is in turn obtained as the sum of the proportion $R_{UVblock}$ determined in the UV blocking filter mode (box 233) and the calculated correction proportion $R_{iUVpass}$. The measurement on the colour field in blocking filter mode is symbolised by box 231 and the measurement values L(o) obtained are symbolised by box 232.

The correction proportion $R_{iUVpass}$ due to fluorescence which has to be determined is generally weakened compared with the value $R_{iWUVpass}$ (Formula 1) calculated on the paper whiteness due to additional absorption in the colour coating and surface effects at the measurement site. It is computed using an empirical model (box 236) based on the known theories of Kubelka-Munk, Saunderson and optionally Neugebauer for halftone colours. As may be seen from Formula 12 below, the calculation is based on the values $R_{UVblock}$ (box 233), $R_{WUVblock}$ (box 234) and $R_{iWUVpass}$ (box 225) as well as various model parameters (box 235). The model is defined by the following formula:

$$R_{iUVpass} = \alpha_0 * r_0 + (1-r_0)*(1-r_2)*\rho_i + /(1-r_2*\rho_i^+) \quad \text{[Formula 4]}$$

Here, $\rho_i^+$ stands for the effective internal reflectivity resulting from the reflectivity of the substrate and the transmission of the colour coating as follows:

$$\rho_i^+ = T_{downwards} * \rho_{iWUVpass} * T_{upwards} \quad \text{[Formula 5]}$$

$$\rho_{iWUVpass} = (R_{iWUVpass} - \alpha_0 * r_0)/((1-r_0)*(1-r_2) + (R_{iWUVpass} - \alpha_0 * r_0)*r_2) \quad \text{[Formula 6]}$$

$R_{iWUVpass}$ was calculated from the measurement on the non-printed substrate using formula 1 and the transmission through the colour coating is calculated from the blocking filter measurements $R_{UVblock}$ and $R_{WUVblock}$ respectively as follows:

$$T_{downwards} = [Ext_{extrapol}(\lambda_{UV})\hat{\phantom{x}}0.5]\hat{\phantom{x}}cfd \qquad [\text{Formula 7}]$$

$$T_{upwards} = [Ext\hat{\phantom{x}}0.5]\hat{\phantom{x}}cfu \qquad [\text{Formula 8}]$$

In these:

$\lambda_{UV}$ means the main wavelength of the UV light source, $T_{downwards}$ means the transmissivity of the colour layer in the light incoming direction at UV wavelength $\lambda_{UV}$ (applies to narrow-band UV excitation, otherwise it would be necessary to use the corresponding integral forms)

$T_{upwards}$ means the transmissivity of the colour layer in the light outgoing direction at fluorescence wavelengths, Ext: means extinction, from Kubelka-Munk with Saunderson correction standard model with S=0, cfd, cfu are empirically determined weighting factors, typical values are cfd=4, cfu=2.5.

The value Ext is calculated as follows:

$$Ext = (\rho_F/\rho_W) \qquad [\text{Formula 9}]$$

where the intermediate values $\rho_W$ and $\rho_F$ are calculated using the following formulas:

$$\rho_W = (R_{WUVblock} - \alpha_0 * r_0)/((1-r_0)*(1-r_2) + (R_{WUVblock} - a_0 * r_0) * r_2) \qquad [\text{Formula 10}]$$

$$\rho_F = (R_{UVblock} - \alpha_0 * r_0)/((1-r_0)*(1-r_2) + (R_{UVblock} - \alpha_0 * r_0) * r_2) \qquad [\text{Formula 11}]$$

Typical values for the parameters used in the Kubelka-Munk formula are $r_0$=0.04, $r_2$=0.6 and $\alpha_0$=0.

The constant values cfd, cfu, $r_0$, $r_2$ and $\alpha_0$ are the above-mentioned model parameters (box 235).

Formulas 4-11 set out above may be summarised as follows:

$$R_{iUVpass} = F(R_{UVblock}, R_{WUVblock}, R_{iWUVpass}, cfd, cfu, r_0, r_2, \alpha_0) \qquad [\text{Formula 12}]$$

From this, it may be seen that the spectral correction factor $R_{iUVpass}$ is determined in full for a measured colour field by the first spectral proportion $R_{UVblock}$ of the total reflection factor measured on the colour field and the corresponding proportion $R_{WUVblock}$ measured on the non-printed substrate and the correction factor $R_{iWUVpass}$ determined for the non-printed substrate as well as the model parameters cfd, cfu, $r_0$, $r_2$ and $\alpha_0$. The proportions $R_{WUVblock}$ and $R_{iWUVpass}$ measured or calculated on the non-printed substrate represent the fluorescence effect of the substrate and hence the above-mentioned characteristic data.

As may be seen from calculation formula 7 above, the UV transmission of the colour layers is characterised by means of extrapolation ($Ext_{extrapol}(\lambda_{UV})$), from the UV blocking filter measurement. Whilst transmission of the colour in the fluorescence range (380-600 nm) for $T_{upwards}$ can be determined directly from the standard model, absorption in the UV range (300-420 nm) for UV sources with $\lambda_{UV}$<380 nm is not directly available because no UV blocking filter measurement data is available here. In this case, the value may be obtained by an appropriate extrapolation (e.g. by means of quadratic polynomial) of the known colour transmission in the UV blocking filter measurement range. Another option would be to use a look-up table with colours typical of the application. The table may be generic or determined by a one-off calibration measurement specific to the application.

As may be seen from the explanations given above, the measuring method proposed by the invention is based on the characterisation of the brightener contained in the substrate with a highly reduced sample set (in the extreme situation, with a single sample, the paper whiteness, as described). Alternatively, the brightener may also be characterised by an external measuring method (e.g. bi-spectral method, UV-cut and a filterless (NoF) measuring device or knowledge of the spectral UV efficiency of the brightener from the manufacturer's data).

Instead of being limited to a measurement on the non-printed substrate, the substrate and its brightener may also be characterised on the basis of corresponding measurements on a (limited) sample set. Some (a few) full tone and/or halftone fields may also be used as the sample set, for example. The characterisation may also be done by taking measurements on appropriate calibration fields of the measurement object amongst others by measurements tinder two types of illuminating light with a different UV proportion. The fields of a print control strip contained on many measurement objects may be used as the calibration fields in this instance. These alternative methods of characterising the substrate naturally mean that the correction model used must be adapted accordingly.

The reflection spectra (spectral reflection factors) measured by means of the known UV blocking filter measuring method are converted on a computerised basis with the aid of the brightener characterisation to any type of excitation light (CIE-A, D50, experimentally determined light box spectra, etc.) (see formula 1). The measuring method proposed by the invention has the advantages of a double measurement and needs these physically but only on a significantly reduced sample set, which speeds up the measuring process by up to 50%.

The measuring method proposed by the invention can be implemented relatively easily in existing devices with interchangeable measuring filters (e.g. SpectroEye) or different light sources (UV and white LED, e.g. iSis) and results in a significantly quicker measuring procedure.

The separate characterisation of the fluorescence spectrum and UV blocking filter measurement obviates the requirement for a good spectral conformance of the lighting spectrum in the device. A very high device conformance can therefore be achieved as a result.

Even existing UV blocking filter measuring devices and measuring sequences may be used. The brightener response of the paper in this case is determined externally to the actual measuring procedure. This may be done with an external measuring device with a known brightener proportion, by a bi-spectral measurement or on the basis of the external paper specification (e.g. from the manufacturer).

It is also of advantage to use the proposed method for applications in an automated colour measuring system for measuring printed colour charts for the calibration of printers. In this case, the precision of the predictions can be increased still further because on the one hand a known set of control patches with full and halftones can be selected for characterising the brightener, and on the other hand the printed colour values (e.g. cmyk) are available. The results can be used to generate colour profiles for different types of light with the aid of a colour management software.

The method is also suitable for print shops. When setting the Job up, especially when measuring a first printed sheet, a full double measurement can be run on the entire object because somewhat more time is available. The complete double measurement is based on a white measurement with and without UV in order to characterise the substrate, and the print control strip is measured in with and without UV. As a minimum, only the substrate measurement with and without UV must be run. With this data, the model parameters for the fluorescence correction are determined. When running the printer in colour mode, the measurement must happen quickly. Only one measuring run per sheet is run without UV. The proposed method is used to calculate the spectral reflection factors with the proportion of fluorescence corresponding to the desired lighting.

Although the present disclosure has been described with reference to exemplary embodiments and implementations thereof, the disclosed methods are not limited to such exemplary embodiments/implementations. Rather, as will be readily apparent to persons skilled in the art from the description provided herein, the disclosed methods are susceptible to modifications, alterations and enhancements without departing from the spirit or scope of the present disclosure. Accordingly, the present disclosure expressly encompasses such modification, alterations and enhancements within the scope hereof.

The invention claimed is:

1. A method for measuring the colour of samples printed on substrates containing brightener, the method comprising the steps of:
  a) determining the total spectral reflection factor $R_i(\lambda)$ of a sample printed on a substrate; and
  b) calculating values characterising the colour of the sample using the total spectral reflection factor $R_i(\lambda)$;
  wherein the total spectral reflection factor $R_i(\lambda)$ is obtained as the sum of a first spectral proportion $R_{UVblock}(\lambda)$ and a spectral correction factor $R_{iUVpass}(\lambda)$;
  wherein the first spectral proportion $R_{UVblock}(\lambda)$ represents the spectral reflection factor of the sample as determined during illumination with essentially UV-free light;
  wherein the spectral correction factor $R_{iUVpass}(\lambda)$ represents the proportion of the total spectral reflection factor $R_i(\lambda)$ of the sample which is determined by the effect of the fluorescence of the brightener only;
  wherein the spectral correction factor $R_{iUVpass}(\lambda)$ is calculated from given or measured characterisation data $R_{iWUVpass}(\lambda)$, $R_{WUVblock}(\lambda)$ of the substrate and/or given or measured characterisation data of the brightener contained in the substrate and from a given spectrum of a freely selectable, virtual type of lighting $E_i(\lambda)$ from the first spectral proportion $R_{UVblock}(\lambda)$; and
  wherein a relative spectral weighting of the spectrum of the selected type of lighting $E_i(\lambda)$ is used to calculate the spectral correction factor $R_{iUVpass}(\lambda)$.

2. The method of claim 1, wherein the characterisation data of the substrate is determined by two reflection factor measurements on a limited set of measurement fields, the two reflection measurements including: (i) a first measurement using illuminating light in the absence of or with a negligible amount of UV light, and (ii) a second measurement with essentially only UV illuminating light.

3. The method of claim 2, wherein the limited set of measurement fields comprises print calibration fields of a print control strip.

4. The method of claim 2, wherein the limited set of measurement fields comprises only a non-printed zone on the substrate.

5. The method of claim 1, wherein the spectral correction factor $R_{iUVpass}(\lambda)$ is calculated by determining the UV transmission of colour layers of the sample from the first spectral proportion $R_{UVblock}(\lambda)$.

6. The method of claim 5, wherein the UV transmission of the colour layers is determined by one of (i) extrapolation, and (ii) a look-up table.

7. The method of claim 1, wherein the spectral correction factor $R_{iUVpass}(\lambda)$ is calculated using the formula:

$$R_{iUVpass} = \alpha_0 * r_0 + (1-r_0)*(1-r_2)*\rho_i^+/(1-r_2*\rho_i^+)$$

wherein $\rho_i^+$ represents an effective internal reflectivity resulting from the reflectivity of the substrate and transmission of the colour layers; and
  wherein $\alpha_0$, $r_0$ and $r_2$ are empirical model parameters.

8. The method of claim 7, wherein the empirical model parameters are derived using a technique selected from the group consisting of: (i) the Kubelka-Munk technique, (ii) the Saunderson technique, (iii) the Neugebauer technique, and (iv) combinations thereof.

9. The method of claim 1, wherein two or more total spectral reflection factors are determined by calculating two or more spectral correction factors for two or more selected types of illuminating light allowing for the characterisation data of the substrate from the first spectral proportion.

10. The method of claim 1, wherein the characterisation data of the substrate and the brightener contained in the substrate are determined with a separate measuring device or using known characterization data of the substrate to calculate the spectral correction factor $R_{iUVpass}(\lambda)$.

11. A method for measuring colour of a sample printed on a substrate containing brightener, the method comprising the steps of:
  a) determining a total spectral reflection factor of the brightener-containing sample printed on the substrate; and
  b) calculating values characterising the colour of the sample using the total spectral reflection factor;
  wherein the total spectral reflection factor is obtained as the sum of a first spectral proportion ($R_{UVblock}(\lambda)$) and a spectral correction factor ($R_{iUVpass}(\lambda)$);
  wherein the first spectral proportion represents a spectral reflection factor of the sample determined during illumination with light consisting essentially of UV-free light;
  wherein the spectral correction factor represents only a proportion of the total spectral reflection factor of the sample determined by the effect of fluorescence of the brightener, and the spectral correction factor is calculated making allowance for characterisation data of: (i) the substrate, (ii) the brightener contained in the substrate, and (iii) the spectrum of a selected type of lighting ($E_i(\lambda)$) from the first spectral proportion;
  wherein the spectral correction factor ($R_{iUVpass}(\lambda)$) is calculated using the formula:

$$R_{iUVpass} = \alpha_0 * r_0 + (1-r_0)*(1-r_2)*\rho_i^+/(1-r_2*\rho_i^+)$$

wherein $\rho_i^+$ represents an effective internal reflectivity resulting from the reflectivity of the substrate and transmission of the colour layers; and
  wherein $\alpha_0$, $r_0$ and $r_2$ are empirical model parameters.

12. The method of claim 11, wherein the empirical model parameters are derived using a technique selected from the group consisting of: (i) the Kubelka-Munk technique, (ii) the Saunderson technique, (iii) the Neugebauer technique, and (iv) combinations thereof.

13. The method of claim 11, wherein the characterisation data of the substrate is determined by two reflection factor measurements on a limited set of measurement fields, the two reflection measurements including: (i) a first measurement using illuminating light in the absence of or with a negligible amount of UV light, and (ii) a second measurement with essentially only UV illuminating light.

14. The method of claim 13, wherein the limited set of measurement fields comprises print calibration fields of a print control strip.

15. The method of claim 13, wherein the limited set of measurement fields comprises only a non-printed zone on the substrate.

16. The method of claim 11, wherein the spectral correction factor $R_{iUVpass}(\lambda)$ is calculated by determining the UV transmission of colour layers of the sample from the first spectral proportion $R_{UVblock}(\lambda)$.

17. The method of claim 16, wherein the UV transmission of the colour layers is determined by one of (i) extrapolation, and (ii) a look-up table.

18. The method of claim 11, wherein two or more total spectral reflection factors are determined by calculating two or more spectral correction factors for two or more selected types of illuminating light allowing for the characterisation data of the substrate from the first spectral proportion.

19. The method of claim 11, wherein the characterisation data of the substrate and the brightener contained in the substrate are determined with a separate measuring device or using known characterization data of the substrate to calculate the spectral correction factor $R_{iUVpass}(\lambda)$.

* * * * *

UNITED STATES PATENT AND TRADEMARK OFFICE
CERTIFICATE OF CORRECTION

| | | |
|---|---|---|
| PATENT NO. | : 7,847,264 B2 | Page 1 of 1 |
| APPLICATION NO. | : 12/136373 | |
| DATED | : December 7, 2010 | |
| INVENTOR(S) | : Mark Wegmuller et al. | |

It is certified that error appears in the above-identified patent and that said Letters Patent is hereby corrected as shown below:

Title Page, Item (75) inventors should read
-- Inventors: Mark Wegmuller, Zurich (CH); Peter Ehbets, Zurich (CH); Beat Frick, Buchs (CH) --.

Signed and Sealed this
Third Day of May, 2011

David J. Kappos
*Director of the United States Patent and Trademark Office*